US010683544B2

(12) United States Patent
Cairns et al.

(10) Patent No.: US 10,683,544 B2
(45) Date of Patent: *Jun. 16, 2020

(54) SEQUENCES ASSOCIATED WITH TDP-43 PROTEINOPATHIES AND METHODS OF USING THE SAME

(71) Applicant: Washington University, St. Louis, MO (US)

(72) Inventors: Nigel J. Cairns, St. Louis, MO (US); Robert H. Baloh, St. Louis, MO (US); Alan Pestronk, St. Louis, MO (US); Michael A. Gitcho, St. Louis, MO (US); Alison M. Goate, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/346,268

(22) Filed: Nov. 8, 2016

(65) Prior Publication Data
US 2017/0067112 A1    Mar. 9, 2017

Related U.S. Application Data

(60) Continuation of application No. 14/514,104, filed on Oct. 14, 2014, now Pat. No. 9,523,128, which is a division of application No. 12/865,659, filed as application No. PCT/US2009/032627 on Jan. 30, 2009, now Pat. No. 8,889,597.

(60) Provisional application No. 61/025,377, filed on Feb. 1, 2008.

(51) Int. Cl.
C12Q 1/6883    (2018.01)
C07K 14/47    (2006.01)

(52) U.S. Cl.
CPC ............ *C12Q 1/6883* (2013.01); *C07K 14/47* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 5,688,511 A * | 11/1997 | Gaynor | C07K 14/4702 424/207.1 |
| 6,566,495 B1 | 5/2003 | Fodor | |
| 6,582,908 B2 * | 6/2003 | Fodor | B01J 19/0046 435/288.3 |
| 6,812,339 B1 | 11/2004 | Venter et al. | |
| 8,889,597 B2 | 11/2014 | Cairns et al. | |
| 9,523,128 B2 * | 12/2016 | Cairns | C12Q 1/6883 |
| 2001/0053519 A1 | 12/2001 | Fodor et al. | |
| 2003/0148360 A1 | 8/2003 | Guire | |
| 2005/0026164 A1 * | 2/2005 | Zhou | C12Q 1/6837 506/4 |
| 2006/0134663 A1 | 6/2006 | Harkin | |
| 2006/0240416 A1 | 10/2006 | Banerjee et al. | |
| 2011/0065600 A1 | 3/2011 | Baloh et al. | |
| 2015/0065384 A1 | 3/2015 | Cairns et al. | |

FOREIGN PATENT DOCUMENTS

WO    2009099941 A2    8/2009
WO    2009099941 A3    10/2009

OTHER PUBLICATIONS

NM_007375.3 (*Homo sapiens* TAR DNA binding protein (TARDBP) mRNA, NCBI Reference Accession Entry, GI 42741653, priority to Nov. 18, 2006) (Year: 2006).*
Buratti et al. (2001) Nuclear factor TDP-43 and SR proteins promote in vitro and in vivo CFTR exon 9 skipping. The EMBO Journal, 20(7):1774-1784 (Year: 2001).*
Office Action dated Mar. 22, 2017 from related Canadian Patent Application No. 2,713,871; 3 pgs.
Arai; TDP-re is a component of ubiquitin-positive tau-negative inclusions in frontotemporal lobar degeneration and amyotrophic lateral sclerosis; Biochem Biophys Res Commun; 2006; 351:602-611.
Neumann; Ubiquitinated TDP-43 in Frontotemporal Lobar Degeneration and Amyotrophic Lateral Sclerosis; Science 2006;314:130-133.
Cairns; TDP-43 in Familial and Sporadic Frontotemporal Lobar Degeneration with Ubiquitin Inclusions; Am J Pathol; 2007;171:227-240.
Mackenzie; Pathological TDP-43 Distinguishes Sporadic Amyotrophic Lateral Sclerosis from Amyotrophic Lateral Sclerosis with SOD1 Mutations; Ann Neural; 2007; 61:427-434.
Siddique; Genetic Aspects of Amyotrophic Lateral Sclerosis; Adv Neurol; 2002; 88:21-32.
Pasinelli; Molecular biology of amyotrophic lateral sclerosis; insights from genetics; Nat Rev Neurosci; 2006; 7:710-723.
Goate; Segregation of a missense mutation in the amyloid precursor protein gene with familial Alzheimer's disease; Nature; 1991; 349:704-706.
Polymeropoulos; Mutation in the a-Synuclein Gene Identified in Families with Parkinson's Disease; Science; 1997; 276:2045-2047.
Hutton; Association of missense and 5;-splice-site mutations in tau with the inherited dementia FTDP-17; Nature; 1998; 393:702-705.
Wang; Structural diversity and functional implications of the eukaryotic TDP gene family; Genomics; 2004; 83:130-139.
Ou; Cloning and Characterization of a Novel Cellular Protein, TDP-43, That Binds to Human Immunodeficiency Virus Type 1 TAR DNA Sequence Motifs; J Virol; 1995; 69:3584-3596.
Buratti; Nuclear factor TDP-43 and SR proteins promote in vitro and in vivo CFTR exon 9 skipping; EMBO J 2001; 20:1774-1784.
Ayala; Human, *Drosophila*, and C. elegans TDP43: Nucleic Acid Binding Properties and Splicing Regulatory Function; J Mol Biol; 2005; 348:575-588.

(Continued)

Primary Examiner — Neil P Hammell
(74) Attorney, Agent, or Firm — Polsinelli PC

(57) ABSTRACT

The present invention provides nucleic acids and peptides, and methods of using the nucleic acids and peptides to identify subjects at risk for a TDP-43 proteinopathy. The invention also provides for an array comprising the nucleic acids and peptides of the invention.

3 Claims, 2 Drawing Sheets
Specification includes a Sequence Listing.

(56) References Cited

OTHER PUBLICATIONS

Cairns; Neuropathologic diagnostic and nosologic criteria for frontotemporal lobar degeneration: consensus of the Consortium for Frontotemporal Lobar Degeneration; Acta Neuropathol; 2007; 114:5-22.
[Book] Strong (editor). Dementia and Motor Neuron Disease. 2006. Informa, Oxford, UK.
Rockett; DNA arrays: technology, options and toxicological applications; Xenobiotica; 2000; 30(2):155-177.
International Search Report and Written Opinion dated Jul. 20, 2009 from related International application No. PCT/US09/32627, 10 pgs.
Translation of Notice of Rejection dated Oct. 8, 2013 from related Japanese Patent Application No. 2010-545202, 3 pgs.
Rollinson, TDP-43 gene analysis in frontotemporal lobar degeneration, ScienceDirect Neuroscience Letters 419, 2007, 1-4.
Translation of Notice of Rejection dated Oct. 7, 2014 from related Japanese Patent Application No. 2010-545202, 3 pgs.
GenBank Record U23731.
Benson, D. et al., "GenBank," Nucleic Acids Res, 2005, pp. D34-D38, vol. 33, Oxford University Press.
GenBank ABO32290.1, "TDP43 [*Homo sapiens*]," Mar. 19, 2007, 1 pg.
GenBank EF434181.1, "*Homo sapiens* TDP43 mRNA, complete cds, alternatively spliced," Mar. 19, 2007, 1 pg.
GenBank AM191777.1, "RZPD MPMGp1172 Paracentrotus lividus MBSB Paracentrotus lividus cDNA clone MPMGp1172K1228Q 5-, mRNA sequence," Mar. 12, 2006, 2 pgs.
Kohara, Y. et al., "DNA probes on beads arrayed in a capillary, 'Bead-array', exhibited high hybridization performance," Nucleic Acids Res., 2002, pp. 1-7, vol. 30, No. 16, Issue e87, Oxford University Press.
Mackenzie, I. et al., "The role of TDP-43 in amyotrophic lateral sclerosis and frontotemporal dementia," NIH Public Access Author Manuscript, Curr. Opi.n. Neural., Dec. 2008, pp. 693-700, vol. 21, No. 6.

NCBI Reference Sequence XM_749311.1, "Aspergillus fumigatus Af293 MFS sugar transporter (AFUA_3G12170), partial mRNA," Feb. 27, 2008, 2 pgs.
NCBI Reference Sequence NM007375.3, "*Homo sapiens* TAR DNA binding protein (TARDBP), mRNA," Nov. 18, 2006, 5 pgs.
Notice of Allowance dated Jul. 16, 2014 from related U.S. Appl. No. 12/865,659; 9 pgs.
Notice of References Cited dated Aug. 8, 2012 from related U.S. Appl. No. 12/865,659; 1 pg.
Notice of Allowance dated Aug. 10, 2016 from related U.S. Appl. No. 14/514,104; 10 pgs.
Office Action dated Mar. 1, 2016 from related Canadian Patent Application No. 2,713,871; 4 pgs.
Office Action dated Jan. 16, 2015 from related Canadian Patent Application No. 2,713,871; 4 pgs.
Office Action dated Nov. 4, 2015 from related Japanese Patent Application No. 2015-019179; 10 pgs., with English translation.
Office Action dated Jul. 5, 2016 from related Japanese Patent Application No. 2015-019179; 10 pgs., with English translation.
Office Action dated Mar. 11, 2014 from related U.S. Appl. No. 12/865,659; 10 pgs.
Office Action dated Aug. 8, 2013 from related U.S. Appl. No. 12/865,659; 11 pgs.
Office Action dated Nov. 16, 2012 from related U.S. Appl. No. 12/865,659; 11 pgs.
Office Action dated Apr. 8, 2016 from related U.S. Appl. No. 14/514,104; 14 pgs.
Office Action dated Dec. 7, 2015 from related U.S. Appl. No. 14/514,104; 13 pgs.
Sambrook, J. et al., "Molecular Cloning: A Laboratory Manual," vol. 1, 3rd Ed., Cold Spring Harbor Laboratory Press, 2001, Chapter 1, pp. 1.152 and Chapter 12, pp. 12.1-12.9, Cold Spring Harbor, New York.
Sambrook et al., 1989 Molecular Cloning, A Laboratory Manual, Cold Spring Harbor Press, N.Y. [Book].
Strong, M. et al., "TDP43 is a human low molecular weight neurofilament (hNFL) mRNA-binding protein," Mol. Cell. Neurosci., 2007, pp. 320-327, vol. 35, Elsevier.
Notice of Allowance dated Oct. 13, 2017 from related Canadian Patent Application No. 2,713,871; 1 pg.

* cited by examiner

SEQUENCES ASSOCIATED WITH TDP-43 PROTEINOPATHIES AND METHODS OF USING THE SAME

CROSS REFERENCE TO RELATED APPLICATIONS

This application claims the priority of U.S. Ser. No. 14/514,104, filed Oct. 14, 2014, which claims the priority of U.S. Ser. No. 12/865,659, filed Nov. 22, 2010, which claims priority to PCT/US09/32627, filed Jan. 30, 2009, which claims priority to U.S. provisional application No. 61/025,377, filed Feb. 1, 2008, which is hereby incorporated by reference in its entirety.

GOVERNMENTAL RIGHTS

This invention was made with government support under P50-AG05681 awarded by the National Institutes of Health. The government has certain rights in the invention.

FIELD OF THE INVENTION

The present invention provides nucleic acid and amino acid sequences that may be utilized to identify subjects at risk for a TDP-43 proteinopathy.

BACKGROUND OF THE INVENTION

TAR DNA-binding protein 43 (TDP-43) is a pathological protein of sporadic and familial frontotemporal lobar degeneration (FTLD) with ubiquitin-positive, tau-negative inclusions (FTLD-U) with or without motor neuron disease (MND). MND is a neurodegenerative disorder involving the loss of upper and/or lower motor neurons and is characterized clinically by progressive weakness and death within a few years of onset; the most common clinical MND phenotype is amyotrophic lateral sclerosis (ALS). Recently, TAR DNA-binding protein 43 (TDP-43) was identified as a pathological protein of the motor neuron inclusions found in sporadic MND, but not in familial MND with Cu/Zn superoxide dismutase-1 (SOD1) mutation.[1-4] TDP-43 thus defines a class of neurodegenerative diseases referred to as TDP-43 proteinopathies. There is a need in the art for understanding the link between TDP-43 and these diseases, such that diagnostic and therapeutic treatments may be developed.

SUMMARY OF THE INVENTION

One aspect of the invention encompasses an isolated nucleic acid comprising at least ten contiguous nucleotides, including nucleotide 1077, of SEQ ID NO:1.

Another aspect of the invention encompasses an isolated peptide comprising at least ten contiguous amino acids, including amino acid 315, of SEQ ID NO:2.

Yet another aspect of the invention encompasses a method for identifying a subject at risk for a TDP-43 proteinopathy. The method comprises determining the identity of the nucleotide at position 1077 of a nucleotide sequence comprising the nucleic acid sequence of SEQ ID NO:1 in a sample from a subject. The presence of a G instead of an A at nucleotide 1077 indicates a risk for a TDP-43 proteinopathy.

An additional aspect of the invention encompasses a method for identifying a subject at risk for a TDP-43 proteinopathy. The method comprises determining the identity of the amino acid at position 315 of an amino acid sequence comprising the amino acid sequence of SEQ ID NO:2 in a sample from a subject. The presence of a threonine instead of an alanine at amino acid 315 indicates a risk for a TDP-43 proteinopathy.

A further aspect of the invention encompasses an array that comprises an address comprising an epitope binding agent. In one iteration, the epitope binding agent can specifically bind to SEQ ID NO:1 or a portion thereof containing nucleotide 1077. Alternatively, the epitope binding agent can specifically bind to SEQ ID NO:2 or a portion thereof containing amino acid 315.

Other aspects and iterations of the invention are described more thoroughly below.

DETAILED DESCRIPTION OF THE INVENTION

Figure 1A:
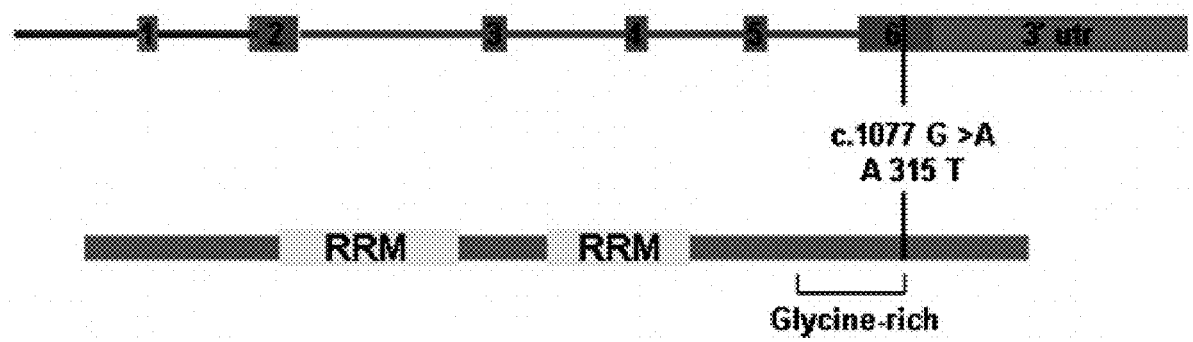
FIG. 1A-C depicts illustrations showing that the missense mutation A315T within a highly conserved region of exon 6 of TDP-43 segregates with all affected members of an autosomal dominant MND family. (a) TDP-43 genomic structure, position of missense mutation, and location of amino acid change adjacent to glycine-rich domain. (b) Chromatogram of exon 6 displays a base pair change (c.1077 G>A) compared to family control. (c) Pedigree of family displays segregation of the mutation with disease (◇=unaffected, ◆=affected with mutation, diagonal line=deceased). RsaI restriction digest was used to screen family members and 1,505 controls. Direct sequencing was also performed on all family members in this study to verify the mutation.

The present invention provides a nucleic acid sequence variant of TDP-43 (SEQ ID NO:1 in Table 1) that is associated with TDP-43 proteinopathies. In particular, nucleic acid 1077 of SEQ ID NO:1 is an A, as opposed to a G. Additionally, the invention provides an amino acid sequence variant (SEQ ID NO:2 in Table 1) of TDP-43 that is associated with TDP-43 proteinopathies. In particular, amino acid 315 of SEQ ID NO:2 is a threonine, as opposed to an alanine. The invention also encompasses methods of diagnosing or detecting a TDP-43 proteinopathy in a subject and an array. The sequences for SEQ ID Nos. 1, 2, 3, and 4 are shown in Table 1 below.

TABLE 1

SEQ ID NO: 1  ggtgggcggggggaggaggcggccctagcgccattttgtgggagcgaagcggtggctgggctgcgcttgggtccgtcgctgctt
cggtgtccctgtcgggcttcccagcagcggcctagcgggaaaagtaaaagatgtctgaatatattcgggtaaccgaagatgaga
acgatgagcccattgaaataccatcggaagacgatgggacggtgctgctctccacggttacagcccagtttccaggggcgtgtg
ggcttcgctacaggaatccagtgtctcagtgtatgagaggtgtccggctggtagaaggaattctgcatgcccagatgctggctgg
ggaaatctggtgtatgttgtcaactatccaaaagataacaaaagaaaaatggatgagacagatgcttcatcagcagtgaaagtg
aaaagagcagtccagaaaacatccgatttaatagtgtttgggtctcccatggaaaacaaccgaacaggacctgaaagagtatttt
agtacctttggagaagttcttatggtgcaggtcaagaaagatcttaagactggtcattcaaagggtttggctttgttcgttttacggaa
tatgaaacacaagtgaaagtaatgtcacagcgacatatgatagatggacgatggtgtgactgcaaacttcctaattctaagcaaa
gccaagatgagcctttgagaagcagaaaagtgtttgtggggcgctgtacagaggacatgactgaggatgagctgcgggagttct
tctctcagtacggggatgtgatggatgtcttcatccccaagccattcagggcctttgcctttgttacatttgcagatgatcagattgcgc
agtctctttgtggagaggacttgatcattaaaggaatcagcgttcatatatccaatgccgaacctaagcacaatagcaatagacag

TABLE 1-continued

```
ttagaaagaagtggaagatttggtggtaatccaggtggctttgggaatcagggtggatttggtaatagcagaggggtggagctg
gtttgggaaacaatcaaggtagtaatatgggtggtgggatgaactttggtacgttcagcattaatccagccatgatggctgccgcc
aggcagcactacagagcagttggggtatgatgggcatgttagccagccagcagaaccagtcaggcccatcgggtaataacca
aaaccaaggcaacatgcagagggagccaaaccaggccttcggttctggaaataactcttatagtggctctaattctggtgcagca
attggttggggatcagcatccaatgcagggtcgggcagtggttttaatggaggctttggctcaagcatggattctaagtcttctggctg
gggaatgtagacagtggggtgtggttggtataggatggtgggaattcaaattttttctaaactcatggtaagtatattgtaaaata
catatgtactaagaattttcaaaattggttgttcagtgtggagtatattcagcagtattttgacatttttctttagaaaaaggaagagcta
aaggaattttataagttttgttacatgaaaggtgaaatattgagtggttgaaagtgaactgctgtttgcctgattggtaaaccaacaca
ctacaattgatatcaaaaggtttctcctgtaatattttatccctggacttgtcaagtgaattcttttgcatgttcaaaacgaaaccattgat
tagaactacattctttaccccttgttttaatttgaaccccaccatatggattttttccttaagaaaatctccttttaggagatcatggtgtca
cagtgtttggttctttgttttgtttttaacacttgtctcccctcatacacaaaagtacaatatgaagccttcatttaatctctgcagttcatct
catttcaaatgtttatgaagaagcacttcattgaaagtagtgctgtaaatattctgccataggaatactgtctacatgctttctcattca
agaattcgtcatcacgcatcacaggccgcgtctttgacggtggggtgtcccattttttatccgctactctttatttcatggagtcgtatcaac
gctatgaacgcaaggctgtgatatggaaccagaaggctgtctgaacttttgaaaccttgtgtgggattgatggtggtgccgaggcat
gaaaggctagtatgagcgagaaaggagagagcgcgtgcagagacttggtggtgcataatggatatttttaacttggcgagatg
tgtctctcaatcctgtggctttggtgagagagtgtgcagagagcaatgatagcaaataatgtacgaatgttttttgcattcaaaggac
atccacatctgttggaagacttttaagtgagttttttgttcttagataacccacattagatgaatgtgttaagtgaaatgatacttgtactcc
ccctaccccttttgtcaactgctgtgaatgctgtatggtggtgtgttctcttctgttactgatatgtaagtgtggcaatgtgaactgaagctga
tgggctgagaacatggactgagctgtggtgtgctttcaggaggacttgaagcagagttcaccagtgagctcaggtgtctcaaag
aagggtggaagttctaatgtctgttagctacccataagaatgctgtttgctgcagttctgtgtcctgtgcttggatgcttttataagagttg
tcattgttggaaattcttaaataaaactgatttaaataatatgtgtctttgttttgcagccctgaatgcaaagaattcatagcagttaattc
cccttttttgacccttttgagatggaactttcataaagtttcttggcagtagttttatttgcttcaaataaacttatttgaaaagttgtctcaagt
caaatggattcatcacctgtcatgcattgacacctgatacccagacttaattggtatttgttcttgcattggccaaagtgaaaattttttttt
ttcttttgaaatctagttttgaataagtctgggtgaccgcacctaaaatggtaagcagtaccctccggctttttcttagtgcctctgtgcatt
tgggtgatgttctatttacatggcctgtgtaaatctccattgggaagtcatgccttctaaaaagattcttatttgggggagtgggcaaaa
tgttgattattttctaatgcttttgtagcaaagcatatcaattgaaaaggaatatcagcaccttcctagtttgggatttgaaaagtggaat
taattgcagtagggataaagtagaagaaaccacaaattatcttgtgcctgaaatccattaagaggcctgatagcttaagaattag
ggtgggttgtctgtctggaagtgttaagtggaatgggctttgtcctccaggaggtgggggaatgtggtaacattgaatacagttgaat
aaaaatcgcttacaaaactcacactctcacaatgcattgttaagtatgtaaaagcaataacattgattctctgtttgtacttttttgtaacta
attctgtgagagttgagctcatttctcagttggaagaatgtgatatttgttgtgtttggtagtttacctaatgccttacctaattagattatgat
aaatatagggtttgtcattttgcaagttacataaacatttatcaatgaagtcatccttagacttgtaatcgccacattgtttcattattcagtttc
ctctgtaaagggatcttgagttgttttaattttttttttctgcatctgaatctgcatgatttccaaacctgtgccatctgaattttgcattttagc
acttgcactattactcagcagcagtaacatggtaacacttaaaatggtactcggggacctccaaagactaaactgacaagccttc
aaggagcccaggggtaagttaacttgtcaacggcatggtttaatccttctttacacttgtgtaaatttcagttactggtcatagaagg
ctttcaatgttgagtggcctttttattaacatgtttatggtactgcatagataccggtatttatttttaccctaagaagattttgaagtttaaaag
tacttaaactatttggcaaagatttgtttttaaaaatctatttggtcaatctaaatgcattcattctaaaaaattttttgaaccagataaata
aaatttttttttgacaccacaaaaaaaaaaaaaaaaaaa
```

SEQ ID NO: 2

```
MSEYIRVTEDENDEPIEIPSEDDGTVLLSTVTAQFPGACGLRYRNPVSQCMRGVRLVEGILH
APDAGWGNLVYVVNYPKDNKRKMDETDASSAVKVKRAVQKTSDLIVLGLPWKTTEQDLKE
YFSTFGEVLMVQVKKDLKTGHSKGFGFVRFTEYETQVKVMSQRHMIDGRWCDCKLPNSKQ
SQDEPLRSRKVFVGRCTEDMTEDELREFFSQYGDVMDVFIPKPFRAFAFVTFADDQIAQSL
CGEDLIIKGISVHISNAEPKHNSNRQLERSGRFGGNPGGFGNQGGFGNSRGGGAGLGNNQ
GSNMGGGMNFGTFSINPAMMAAAQAALQSSWGMMGMLASQQNQSGPSGNNQNQGNM
QREPNQAFGSGNNSYSGSNSGAAIGWGSASNAG SGSGFNGGFGSSMDSKSSGWGM
```

SEQ ID NO: 3

```
ggtgggcgggggagggggcggccctagcgccattttgtgggagcgaagcggtggctgggctgcgcttgggtccgtcgctgctt
cggtgtccctgtcgggcttcccagcagcggcctagcgggaaaagtaaaagatgtctgaatatattcgggtaaccgaagatgaga
cggatgagcccattgaaataccatcggaagacgatgggacggtgctgctctccacggttacagcccagtttccaggggcgtgtg
ggcttcgctacaggaatccagtgtctcagtgatgcaggagggtgccggctggtagaaggaattctgcatgccccagatgctggctgg
ggaaatctggtgtatgttgtcaactatccaaaagataacaaaagaaaaatggatgagacagatgcttcatcagcagtgaaaagtg
aaaagagcagtccagaaaacatccgatttaatagtgttgggtctcccatgaaaacaaccgaacaggacctgaaagagtatttt
agtacctttggagaagttcttatggtgcaggtcaagaaagatcttaagactggtcattcaaagggttttggctttgttcgttttacggaa
tatgaaacacaagtgaaagtaatgtcacagcgacatatgatagatggacggtggtgactgcaaacttcctaattctaagcaaa
gccaagatgagccttcgagaagcagaaaagtgtttgtggggcgctgtacagaggacatgactgaggatgagctgcgggagtct
tctctcagtacggggatgtgatggatgtcttcatccccaagccattcagggcctttgcctttgttacatttgcagatgatcagattgcgc
agtctctttgtggagaggacttgatcattaaaggaatcagcgttcatatatccaatgccgaacctaagcacaatagcaatagacag
ttagaaagaagtggaagatttggtggtaatccaggtggctttgggaatcagggtggatttggtaatagcagaggggtggagctg
gtttgggaaacaatcaaggtagtaatatgggtggtgggatgaactttggtacgttcagcattaatccagccatgatggctgccgcc
aggcagcactacagagcagttggggtatgatgggcatgttagccagccagcagaaccagtcaggcccatcgggtaataacca
aaaccaaggcaacatgcagagggagccaaaccaggccttcggttctggaaataactcttatagtggctctaattctggtgcagca
attggttggggatcagcatccaatgcagggtcgggcagtggttttaatggaggctttggctcaagcatggattctaagtcttctggctg
gggaatgtagacagtggggtgtggttggtataggatggtgggaattcaaattttttctaaactcatggtaagtatattgtaaaata
catatgtactaagaattttcaaaattggttgttcagtgtggagtatattcagcagtattttgacatttttctttagaaaaaggaagagcta
aaggaattttataagttttgttacatgaaaggtgaaatattgagtggttgaaagtgaactgctgtttgcctgattggtaaaccaacaca
ctacaattgatatcaaaaggtttctcctgtaatattttatccctggacttgtcaagtgaattcttttgcatgttcaaaacgaaaccattgat
tagaactacattctttaccccttgttttaatttgaaccccaccatatggattttttccttaagaaaatctccttttaggagatcatggtgtca
cagtgtttggttctttgttttgtttttaacacttgtctcccctcatacacaaaagtacaatatgaagccttcatttaatctctgcagttcatct
catttcaaatgtttatgaagaagcacttcattgaaagtagtgctgtaaatattctgccataggaatactgtctacatgctttctcattca
agaattcgtcatcacgcatcacaggccgcgtctttgacggtggggtgtcccattttttatccgctactctttatttcatggagtcgtatcaac
gctatgaacgcaaggctgtgatatggaaccagaaggctgtctgaacttttgaaaccttgtgtgggattgatggtggtgccgaggcat
gaaaggctagtatgagcgagaaaggagagagcgcgtgcagagacttggtggtgcataatggatatttttaacttggcgagatg
tgtctctcaatcctgtggctttggtgagagagtgtgcagagagcaatgatagcaaataatgtacgaatgttttttgcattcaaaggac
atccacatctgttggaagacttttaagtgagttttttgttcttagataacccacattagatgaatgtgttaagtgaaatgatacttgtactcc
ccctaccccttttgtcaactgctgtgaatgctgtatggtggtgtgttctcttctgttactgatatgtaagtgtggcaatgtgaactgaagctga
tgggctgagaacatggactgagctgtggtgtgctttcaggaggacttgaagcagagttcaccagtgagctcaggtgtctcaaag
aagggtggaagttctaatgtctgttagctacccataagaatgctgtttgctgcagttctgtgtcctgtgcttggatgcttttataagagttg
tcattgttggaaattcttaaataaaactgatttaaataatatgtgtctttgttttgcagccctgaatgcaaagaattcatagcagttaattc
cccttttttgacccttttgagatggaactttcataaagtttcttggcagtagttttatttgcttcaaataaacttatttgaaaagttgtctcaagt
caaatggattcatcacctgtcatgcattgacacctgatacccagacttaattggtatttgttcttgcattggccaaagtgaaaattttttttt
```

TABLE 1-continued

```
ttcttttgaaatctagttttgaataagtctgggtgaccgcacctaaaatggtaagcagtaccctccggcttttcttagtgcctctgtgcatt
tgggtgatgttctatttacatggcctgtgtaaatctccattgggaagtcatgccttctaaaaagattcttatttgggggagtgggcaaaa
tgttgattattttctaatgctttgtagcaaagcatatcaattgaaaagggaatatcagcaccttcctagtttgggatttgaaaagtggaat
taattgcagtagggataaagtagaagaaaccacaaattatcttgtgcctgaaatccattaagaggcctgatagctttaagaattag
ggtgggttgtctgtctggaagtgttaagtggaatgggctttgtcctccaggaggtggggaatgtggtaacattgaatacagttgaat
aaaatcgcttacaaaactcacactctcacaatgcattgttaagtatgtaaaagcaataacattgattctctgttgtacttttttgtaacta
attctgtgagagttgagctcattttctagttggaagaatgtgatatttgttgtgttggtagtttacctaatgcccttacctaattagattatgat
aaataggtttgtcattttgcaagttacataaacatttatcaatgaagtcatccttagacttgtaatcgccacattgtttcattattcagtttc
ctctgtaaagggatcttgagttgttttaattttttttttctgcatctgaatctgcatgatttccaaaccctgtaccatctgaattttgcattttagc
acttgcactattactcagcagcagtaacatggtaacacttaaaatggtactcggggacctccaaagactaaactgacaagccttc
aaggagcccaggggtaagttaacttgtcaacggcatggtttaatcccttctttacacttgtgtaaatttcagttactggtcatagaagg
ctttcaatgttgagtggcctttattaacatgtttatggtactgcatagatacgggtatttattttaccctaagaagattttgaagtttaaaag
tacttaaactatttggcaaagatttgttttaaaaatctatttggtcaatctaaatgcattcattctaaaaaattttttgaaccagataaata
aaatttttttttgacaccacaaaaaaaaaaaaaaaaaaaaa
```

SEQ ID MSEYIRVTEDENDEPIEIPSEDDGTVLLSTVTAQFPGACGLRYRNPVSQCMRGVRLVEGILH  
NO: 4 APDAGWGNLVYVVNYPKDNKRKMDETDASSAVKVKRAVQKTSDLIVLGLPWKTTEQDLKE  
YFSTFGEVLMVQVKKDLKTGHSKGFGFVRFTEYETQVKVMSQRHMIDGRWCDCKLPNSKQ  
SQDEPLRSRKVFVGRCTEDMTEDELREFFSQYGDVMDVFIPKPFRAFAFVTFADDQIAQSL  
CGEDLIIKGISVHISNAEPKHNSNRQLERSGRFGGNPGGFGNQGGFGNSRGGGAGLGNNQ  
GSNMGGGMNFGAFSINPAMMAAAQAALQSSWGMMGMLASQQNQSGPSGNNQNQGNM  
QREPNQAFGSGNNSYSGSNSGAAIGWGSASNAGSGSGFNGGFGSSMDSKSSGWGM

I. Nucleic Acid

One aspect of the present invention encompasses an isolated nucleic acid. Generally speaking, the sequence of the nucleic acid comprises nucleotide position 1077 of SEQ ID NO:1. In particular, the sequence of the nucleic acid comprises an A at position 1077 of SEQ ID NO:1, as opposed to the wild-type sequence that has a G at position 1077 (SEQ ID NO:3, Table 1). In one embodiment, the nucleic acid comprises at least five contiguous nucleotides, including nucleotide 1077, of SEQ ID NO:1. In another embodiment, the nucleic acid comprises at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, or at least 100 contiguous nucleotides, including nucleotide 1077, of SEQ ID NO:1. In yet another embodiment, the nucleic acid comprises at least 200, at least 300, at least 400, at least 500, at least 600, at least 700, at least 800, at least 900, or at least 1000 contiguous nucleotides, including nucleotide 1077, of SEQ ID NO:1. In a further embodiment, the nucleic acid comprises at least 1000, at least 2000, at least 3000, at least 4000, or more than 4000 contiguous nucleotides, including nucleotide 1077, of SEQ ID NO:1.

In an alternative embodiment, the nucleic acid comprises exon 6 of TDP-43, wherein nucleic acid 1077 is an A instead of a G. In another alternative embodiment, the nucleic acid comprises the cDNA of TDP-43, wherein nucleic acid 1077 is an A instead of a G. In certain embodiments, the nucleic acid consists of the nucleic acid sequence of SEQ ID NO:1.

The present invention also encompasses nucleic acids that are complementary to the isolated nucleic acid sequences described above. For instance, in some embodiments, a nucleic acid of the invention hybridizes to a nucleic acid comprising nucleotide position 1077 of SEQ ID NO:1. In other embodiments, the nucleic acid hybridizes to a nucleic acid comprising nucleotide 1077 of SEQ ID NO:1 but not to a nucleic acid comprising nucleotide 1077 of SEQ ID NO:3. In one embodiment, the nucleic acid hybridizes to a nucleic acid comprising exon 6 of TDP-43, wherein nucleic acid 1077 is an A instead of a G.

Hybridization of nucleic acids is typically performed under stringent conditions. Nucleic acid duplex or hybrid stability is expressed as the melting temperature or Tm, which is the temperature at which a probe dissociates from a target DNA. This melting temperature is used to define the required stringency conditions. To maximize the rate of annealing of the probe with its target, hybridizations are generally carried out at a temperature that is about 20 to 25° C. below the Tm. For instance, stringent conditions may typically involve hybridizing at about 68° C. in 5×SSC/5× Denhardt's solution/1.0% SDS, and washing in 0.2×SSC/ 0.1% SDS at about 68° C. Moderately stringent conditions include washing in 3×SSC at 42° C. The parameters of salt concentration and temperature can be varied to achieve the optimal level of identity between the nucleic acid and the target sequence, for instance, a sequence comprising nucleotide 1077 of SEQ ID NO:1. One skilled in the art will appreciate which parameters to manipulate to optimize hybridization. Additional guidance regarding such conditions is readily available in the art, for example, by Sambrook et al., 1989, Molecular Cloning, A Laboratory Manual, Cold Spring Harbor Press, N.Y.; and Ausubel et al., (eds.), 1995, Current Protocols in Molecular Biology, (John Wiley & Sons, N.Y.) at Unit 2.10.

The isolated nucleic acids of the invention may be labeled. Non-limiting examples of suitable labels may include fluorescent labels, chemiluminescent labels, radioactive labels, colorimetric labels, and resonance labels. Methods of labeling nucleic acids are well known in the art.

The various nucleic acids mentioned above may be obtained using a variety of different techniques known in the art. The nucleic acids may be isolated using standard techniques, may be synthesized using standard techniques, or may be purchased or obtained from a depository. Once the nucleic acid is obtained, it may be amplified and/or sequenced for use in a variety of applications, e.g. the methods described below.

The invention also encompasses production of nucleic acids comprising nucleotide 1077 of SEQ ID NO:1, or derivatives or fragments thereof, that may be made by any method known in the art, including by synthetic chemistry. After production, the synthetic sequence may be inserted into any of the many available expression vectors and cell systems using reagents well known in the art.

II. Peptide

Another aspect of the present invention encompasses an isolated peptide. Generally speaking, the amino acid sequence of the peptide comprises the amino acid at position 315 of SEQ ID NO:2. In particular, the sequence of the peptide comprises threonine at position 315 of SEQ ID NO:2, as opposed to the wild-type sequence that has an alanine at position 315 (SEQ ID NO:4 in Table 1). In one embodiment, the peptide comprises at least five contiguous amino acids, including amino acid 315, of SEQ ID NO:2. In another embodiment, the peptide comprises at least 10, at least 15, at least 20, at least 25, at least 30, at least 35, at least 40, at least 45, at least 50, at least 55, at least 60, at least 65, at least 70, at least 75, at least 80, at least 90 or at least 100 contiguous amino acids, including amino acid 315, of SEQ ID NO:2. In yet another embodiment, the peptide comprises at least 200, at least 300, at least 400 or at least 500 contiguous amino acids, including amino acid 315, of SEQ ID NO:2.

In an alternative embodiment, the peptide comprises the translated amino acid sequence of exon 6 of TDP-43, wherein amino acid 315 is a threonine. In yet another alternative, the peptide consists of the amino acid sequence of TDP-43, wherein amino acid 315 is a threonine.

The isolated peptide of the invention may be labeled. Non-limiting examples of suitable labels include fluorescent labels, chemiluminescent labels, radioactive labels, colorimetric labels, and resonance labels. Methods of labeling peptides are well known in the art.

The various peptides mentioned above may be obtained using a variety of different techniques known in the art. The peptides may be isolated using standard techniques, may be synthesized using standard techniques, or may be purchased or obtained from a depository.

The invention also encompasses production of peptides comprising amino acid 315 of SEQ ID NO:2, or derivatives or fragments thereof, that may be made by any method known in the art, including by synthetic chemistry.

III. Methods

Yet another aspect of the invention encompasses methods for determining risk and diagnosis of a TDP-43 proteinopathy. As used herein, a TDP-43 proteinopathy is a disorder or a disease characterized in part by a mutation or malfunction of the TDP-43 protein. In an exemplary embodiment, a TDP-43 proteinopathy is a disease or a disorder characterized in part by the substitution of the guanine at nucleotide 1077 of SEQ ID NO:3 to an adenine resulting in the nucleic acid sequence variant of SEQ ID NO:1, or the substitution of the alanine at amino acid 315 of SEQ ID NO:4 to a threonine resulting in the amino acid sequence variant of SEQ ID NO:2. Non-limiting examples of a TDP-43 proteinopathy may include sporadic frontotemporal lobar degeneration (FTLD), also called frontotemporal dementia, familial FTLD, sporadic MND, familial MND, sporadic ALS, and familial ALS, and combinations of these two motor and cognitive phenotypes, including FTLD-MND.

In one embodiment, the invention provides a method for determining whether a subject is at risk for a TDP-43 proteinopathy. For instance, in some embodiments, the invention provides a method for determining whether a subject is at risk for ALS. Generally speaking, the method comprises determining whether the subject has an adenine at nucleotide 1077 of TDP-43 instead of a guanine. If an adenine is present, the subject may be at risk for developing a TDP-43 proteinopathy. Alternatively, the method may comprise determining whether the subject has a threonine at amino acid 315 of TDP-43 instead of an alanine. If a threonine is present, the subject may be at risk for developing a TDP-43 proteinopathy.

In another embodiment, the invention provides a method for diagnosing a subject with a TDP-43 proteinopathy. For instance, in some embodiments, the invention provides a method for diagnosing a subject with ALS. Typically, the method comprises determining whether the subject has an adenine at nucleotide 1077 of TDP-43 instead of a guanine. If an adenine is present, the subject may be diagnosed with a TDP-43 proteinopathy. Alternatively, the method may comprise determining whether the subject has a threonine at amino acid 315 of TDP-43 instead of an alanine. If a threonine is present, the subject may be diagnosed with a TDP-43 proteinopathy.

Methods for determining whether a subject has an adenine at nucleotide 1077 of TDP-43 instead of a guanine are known in the art. For instance, sequencing of a portion of TDP-43 encompassing nucleotide 1077 may be performed as detailed in the examples. Alternatively, an array may be used as detailed below.

Figure 1B:
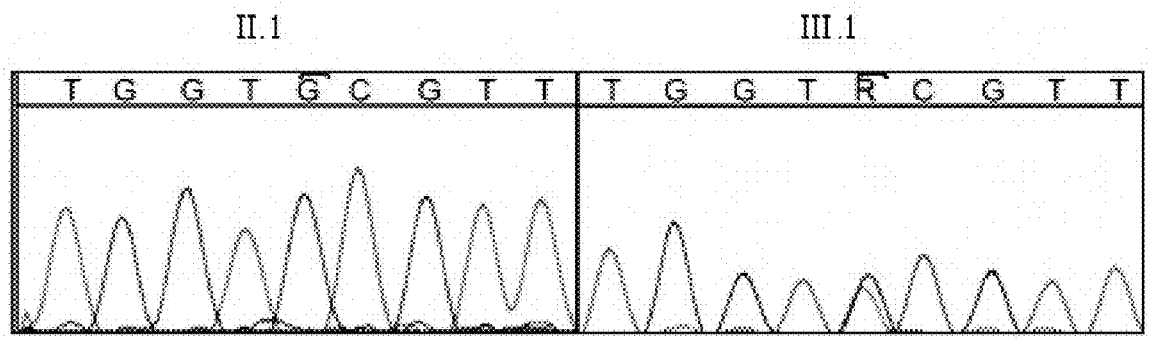
Figure 1C:
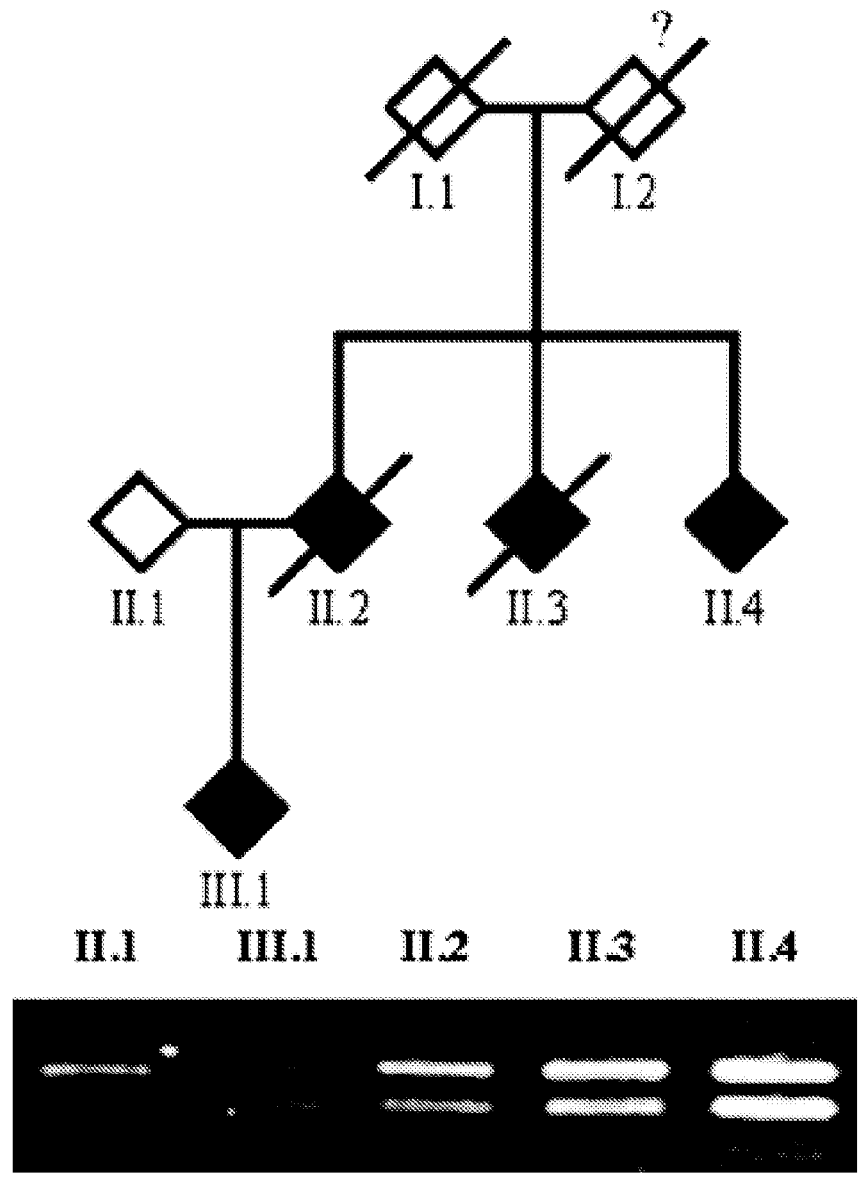

In certain embodiments, nucleic acid from a subject may be digested with a restriction enzyme that generates a unique fragment in a subject with an adenine at nucleotide 1077 of TDP-43 instead of a guanine. For instance, the restriction enzyme Rsa1 may be used. Rsa1 generates a unique fragment when incubated with a nucleic acid comprising exon 6 of TDP-43 when nucleotide 1077 is an adenine. The fragment may be amplified from genomic DNA using the polymerase chain reaction method. For instance, see FIG. 1C.

Similarly, methods for determining whether a subject has a threonine at amino acid 315 of TDP-43 instead of an alanine are known in the art. For instance, an array may be used as detailed below. Alternatively an antibody that recognizes a threonine at position 315, but not an alanine, may be used.

Methods of obtaining a nucleic acid and/or a peptide of the invention from a subject are known in the art. For instance, biological samples comprising a nucleic acid and/ or a peptide of the invention may be collected from a subject. Non-limiting examples of suitable biological samples may include blood samples, tissues samples, or bodily fluid samples. Blood samples may include whole blood, serum, or plasma. Bodily fluid samples may include urine, lymph, or saliva samples.

Suitable subjects express TDP-43. For instance, humans, non-human primates, rodents, livestock animals, and companion animals are non-limiting examples of suitable subjects. Rodents may include mice, rats, and guinea pigs. Livestock animals may include cattle, swine, and chicken. Companion animals may include cats and dogs. In some embodiments, the subject is a frog. In each of the above embodiments, the subject may have a family history of a TDP-43 proteinopathy, of a MND, or of FTLD. Alternatively, the subject may have symptoms of a TDP-43 proteinopathy, of a MND, or of a FTLD. In some embodiments, the subject may have no clinical symptoms of a TDP-43 proteinopathy, of a MND, or of a FTLD.

IV. Array

A further aspect of the invention is an array comprising at least one address. In some embodiments, at least one address of the array has disposed thereon an epitope binding agent that can specifically bind to SEQ ID NO:1, or a portion thereof, containing nucleotide 1077. In other embodiments, at least one address of the array has disposed thereon an epitope binding agent that can specifically bind to SEQ ID NO: 2, or a portion thereof, containing amino acid 315.

Several substrates suitable for the construction of arrays are known in the art, and one skilled in the art will appreciate that other substrates may become available as the art progresses. The substrate may be a material that may be modified to contain discrete individual sites appropriate for the attachment or association of an epitope binding agent and is amenable to at least one detection method. Non-limiting examples of substrate materials include glass, modified or functionalized glass, plastics (including acrylics, polystyrene and copolymers of styrene and other materials, polypropylene, polyethylene, polybutylene, polyurethanes, TeflonJ, etc.), nylon or nitrocellulose, polysaccharides, nylon, resins, silica or silica-based materials including silicon and modified silicon, carbon, metals, inorganic glasses and plastics. In an exemplary embodiment, the substrate may allow optical detection without appreciably fluorescing.

A substrate may be planar, a substrate may be a well, i.e. a 364 well plate, or alternatively, a substrate may be a bead. Additionally, the substrate may be the inner surface of a tube for flow-through sample analysis to minimize sample volume. Similarly, the substrate may be flexible, such as a flexible foam, including closed cell foams made of particular plastics.

An epitope binding agent may be attached to the substrate in a wide variety of ways, as will be appreciated by those in the art. The nucleic acid or epitope binding agent may either be synthesized first, with subsequent attachment to the substrate, or may be directly synthesized on the substrate. The substrate and the epitope binding agent may be derivatized with chemical functional groups for subsequent attachment of the two. For example, the substrate may be derivatized with a chemical functional group including, but not limited to, amino groups, carboxyl groups, oxo groups or thiol groups. Using these functional groups, the epitope binding agent may be attached using functional groups on the nucleic acid or epitope binding agent either directly or indirectly using linkers.

The epitope binding agent may also be attached to the substrate non-covalently. For example, a biotinylated epitope binding agent may be prepared, which may bind to surfaces covalently coated with streptavidin, resulting in attachment. Alternatively, an epitope binding agent may be synthesized on the surface using techniques such as photopolymerization and photolithography. Additional methods of attaching epitope binding agents to arrays and methods of synthesizing biomolecules on substrates are well known in the art, i.e. VLSIPS technology from Affymetrix (e.g., see U.S. Pat. No. 6,566,495, and Rockett and Dix, Xenobiotica 30(2):155-177, both of which are hereby incorporated by reference in their entirety).

In one embodiment, the epitope binding agent attached to the substrate is located at a spatially defined address of the array. Arrays may comprise from about 1 to about several hundred thousand addresses. In one embodiment, the array may be comprised of less than 10,000 addresses. In another alternative embodiment, the array may be comprised of at least 10,000 addresses. In yet another alternative embodiment, the array may be comprised of less than 5,000 addresses. In still another alternative embodiment, the array may be comprised of at least 5,000 addresses. In a further embodiment, the array may be comprised of less than 500 addresses. In yet a further embodiment, the array may be comprised of at least 500 addresses.

An epitope binding agent may be represented more than once on a given array. In other words, more than one address of an array may be comprised of the same epitope binding agent. In some embodiments, two, three, or more than three addresses of the array may be comprised of the same epitope binding agent. In certain embodiments, the array may comprise control epitope binding agents and/or control addresses. The controls may be internal controls, positive controls, negative controls, or background controls.

As used herein, "epitope binding agent" may refer to a nucleic acid, an oligonucleic acid, an amino acid, a peptide, a polypeptide, a protein, a lipid, a metabolite, a small molecule or a fragment thereof that recognizes and is capable of binding to SEQ ID NO: 2 or a portion thereof containing amino acid 315, or to SEQ ID NO:1 or a portion thereof containing nucleic acid 1077. Nucleic acids may include RNA, DNA, and naturally occurring or synthetically created derivatives.

In further embodiments, an epitope binding agent of the array may recognize mutations in one or more of the sequences selected from the group of sequences comprising the vesicle-associated membrane protein-associated protein B (VAPB), dynactin (DCTN1), alsin (ALS2), immunoglobulin μ binding protein 2 (IGHMBP2), or glycyl-tRNA synthetase (GARS) genes that are associated with MND.

The arrays may be utilized in several suitable applications. For example, the arrays may be used in methods for detecting association between an epitope binding agent and a target. As used herein, "target" refers to a nucleic acid comprising nucleotide 1077 of SEQ ID NO:1 or a peptide comprising amino acid 315 of SEQ ID NO:2. This method typically comprises incubating a sample comprising a target with the array under conditions such that the target may associate with the epitope binding agent attached to the array. The association may then be detected, using means commonly known in the art, such as fluorescence. "Association," as used in this context, may refer to hybridization, covalent binding, or ionic binding. A skilled artisan will appreciate that conditions under which association may occur will vary depending on the epitope binding agent, the substrate, the sample, and the detection method utilized. As such, suitable conditions may have to be optimized for each individual array created.

In yet another embodiment, the array may be used as a tool in a method for determining whether a subject is at risk for developing a TDP-43 proteinopathy. Similarly, the array may be used as a tool in a method for determining whether a subject is at risk for a MND. Alternatively, the array may be used as a tool in a method for determining whether a subject is at risk for ALS. In another alternative, the array may be used as a tool in a method for determining whether a subject is at risk for FTLD. Typically, such a method comprises incubating the array with a biological sample from the subject. If the biological sample comprises a nucleic acid comprising nucleotide 1077 of SEQ ID NO:1, or a peptide comprising amino acid 315 of SEQ ID NO:2, then an association between the array and the sample may be detected, and the subject may be at risk for developing a TDP-43 proteinopathy.

In certain embodiments, the array may be used as a tool in a method for diagnosing a subject with a TDP-43 proteinopathy. Similarly, the array may be used as a tool in a method for diagnosing a subject with a MND. Alternatively, the array may be used as a tool in a method for diagnosing a subject with ALS. In another alternative, the array may be used as a tool in a method for diagnosing a subject with a FTLD. Typically, such a method comprises incubating the array with a biological sample from the subject. If the biological sample comprises a nucleic acid comprising nucleotide 1077 of SEQ ID NO:1, or a peptide comprising amino acid 315 of SEQ ID NO:2, then an association between the array and the sample may be detected, and the subject may be diagnosed with a TDP-43 proteinopathy.

In each of the above embodiments, the subject may not display clinical signs of MND, ALS, or FTLD. In some embodiments, the subject may display only a few clinical signs of MND, ALS or FTLD.

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

The following examples illustrate various iterations of the invention.

Methods

Genetic analysis. High molecular weight DNA was extracted from whole blood, serum or brain tissue according to standard procedures. DNA from serum was whole-genome amplified using the REPLI-g® Midi Kit (Qiagen Inc., Valencia, Calif., USA) prior to genetic analysis. DNA from a single affected individual from each family was used for sequencing of TDP-43. All exons and the intron-exon boundaries of the TDP-43 gene were amplified using gene specific intronic primers. Direct sequencing of the amplified fragments was performed using the Big Dye Terminator Cycle Sequencing Ready Reaction Kit (Applied Biosystems, Wellesley, Mass., USA) and standard protocols. For most of the fragments the primers used for sequencing were the same as those used for PCR amplification. Reactions were run on an ABI3130 and mutation analysis was performed using Sequencher software v4.6 (Gene Codes Corporation, Ann Arbor, Mich., USA). Positive calls for sequence variants were made only if the variant was observed in both forward and reverse sequence reads. Where possible, sequence variants were tested for segregation with the disease and screened in a set of 1,505 unrelated ethnically-matched controls.

Example 1: Screening

Mutation analysis of the TDP-43 gene was undertaken in 8 families with MND/ALS with an autosomal dominant pattern of inheritance and no mutation within the SOD1 gene, 5 families with familial FTLD-MND, and 25 families with FTLD-U.[14] All families were of European descent. No sporadic cases of MND were available, but additional sporadic cases of FTLD-MND (n=6) and FTLD-U (n=28) were investigated.

This analysis led to the identification of a missense mutation, Ala-315-Thr (c.1077G>A) within exon 6. In TDP-43 this alanine residue is highly conserved throughout the evolutionary spectrum from *Homo sapiens* to *Xenopus tropicalis*, supporting its likely functional importance (Table 2). The A315T mutation segregated with all affected members of an autosomal dominant MND family (additional non-coding sequence variants were also identified in cases with FTLD-U, FTLD-MND, and MND see FIGS. 1*b* & *c* and Table 3). This mutation was absent from a large series of ethnically matched elderly controls (n=1,505).

The phenotype of the four affected family members with the TDP-43 A315T mutation involved a slowly progressive lower motor neuron degeneration syndrome with respiratory involvement, with only minimal involvement of upper motor or bulbar neurons and absence of dementia (Table 3). Brain autopsy in this kindred remains to be undertaken. Similar clinical phenotypes have been reported in sporadic MND and in kindreds with SOD1 mutations.[5,6] The TDP-43 mutation in familial MND reported here supplements other familial neurodegenerative conditions that affect predominantly lower motor neurons including mutations in the vesicle-associated membrane protein-associated protein B (VAPB), dynactin (DCTN1), alsin (ALS2), immunoglobulin µ binding protein 2 (IGHMBP2), and glycyl-tRNA synthetase (GARS) genes, and other mutations in juvenile MND, although some of these mutations have been identified in motor neuron diseases and hereditary motor neuropathies with variable clinical phenotypes.[15]

These data have important implications for both sporadic and familial forms of MND and FTLD-U, which are linked by a common molecular pathology: TDP-43 proteinopathy. The discovery of a missense mutation in TDP-43 in a family with dominantly inherited MND provides evidence of a direct link between TDP-43 function and neurodegeneration.

Example 2: Clinical Family Analysis

The proband (subject III-1 of FIG. 1*d*)) developed weakness and atrophy of his right hand at age 48 years. Leg strength, mental status, cranial nerves, sensory examination, reflexes, coordination and gait were normal at initial examination; upper motor neuron findings were absent. Motor and sensory nerve conduction was normal, but electromyography (EMG) showed denervation in the arms both proximally and distally, with fasciculation potentials in the legs, and occasional large motor unit potentials. Magnetic resonance imaging (MRI) of brain and spinal cord were normal, as was blood work including absent anti-GM1 antibodies; SOD1 gene testing was normal. Three years later his upper extremity weakness had progressed but mental status, cranial nerve function, leg strength, and sensation remained normal.

The proband's father (subject II-2) developed a left foot drop at age 72. Exam showed atrophy and distal weakness in the left foot, fasciculations, and increased deep tendon reflexes without other abnormalities. EMG revealed widespread fasciculations with denervation changes in the legs and paraspinous muscles. Weakness steadily progressed to involve all four extremities with respiratory and swallowing difficulty, and he died of respiratory compromise seven years after diagnosis.

Subject II-3 developed left foot drop at age 64, which progressed to involve both legs and his arms within two years. Examination at age 69 showed symmetric proximal and distal weakness in the upper extremities, with asymmetric (left>right) distal predominant weakness in the legs. Reflexes were brisk throughout. Electrophysiology showed normal sensory and motor nerve conduction, with denervation changes in both the upper and lower extremities. Respiratory weakness developed at age 72 years, and he died of respiratory complications at age 73 years.

Subject II-4 developed right leg weakness at age 83, which progressed to involve both legs requiring wheelchair dependence within two years. Asymmetric arm weakness and respiratory weakness developed at age 85 and at age 86 there was severe atrophy and weakness in the lower and upper extremities with widespread fasciculations.

For more details, see Table 4.

TABLE 2

TDP-43 protein (291-340 amino acids) displays high similarity between species. Residues underlined indicate differences when compared to humans. TDP-43 A315T location is indicated in bold italic.

| Species | 291-340 | SEQ. ID NO. |
|---|---|---|
| Homo sapiens | NSRGGGAGLGNNQGSNM--GGGMNFG*A* FSINPAMMAAAQAALQSSWGMMGML | 5 |

TABLE 2-continued

TDP-43 protein (291-340 amino acids) displays high similarity between species. Residues underlined indicate differences when compared to humans. TDP-43 A315T location is indicated in bold italic.

| Species | 291-340 | SEQ. ID NO. |
|---|---|---|
| Pan troglodytes | NSRGGGAGLGNNQGSNM--GGGMNFG*A*FSINPAMMAAAQAALQSSWGMMGML | 6 |
| Macaca mulatta | NSRGGGAGLGNNQGSNM--GGGMNFG*A*FSINPAMMAAAQAALQSSWGMMGML | 7 |
| Bos Taurus | NSRGGGAGLGNNQGSNM--GGGMNFG*A*FSINPAMMAAAQAALQSSWGMMGML | 8 |
| Felis catus | NSRGGGAGLGNNQGSNM--GGGMNFG*A*FSINPAMMAAAQAALQSSWGMMGML | 9 |
| Cavia porcellus | N-RGGGAGLGNNQGSNM--GGGMNFG*A*FSINPAMMAAAQAALQSSWGMMGML | 10 |
| Rattus norvegicus | NSRGGGAGLGNNQG_G_NM--GGGMNFG*A*FSINPAMMAAAQAALQSSWGMMGML | 11 |
| Mus musculus | NSRGGGAGLGNNQGGNM--GGGMNFG*A*FSINPAMMAAAQAALQSSWGMMGML | 12 |
| Gallus gallus | NSRGGG_G_GLGNNQGSNM--GGGMNFG*A*FSINPAMMAAAQAALQSSWGMMGML | 13 |
| Xenopus tropicalis | NSR_PSS_GALGNNQG_G_NMGGGGGMNFG*A*FSINPAMMAAAQAALQSSWGMMGML | 14 |

TABLE 3

| Position | Region | Nucleotide change | Amino acid | Pathological entities | Frequency |
|---|---|---|---|---|---|
| c.1-430 | 5'UTR | G > A | n/a | MND | 0.04a |
| c.332 | Ex 2 | T > C | A 66 A | MND, FTLD-MND, control | 0.01087b |
| c.848 + 69 | In 5-6 | `+/G | n/a | MND, FTLD-MND, FTLD-U, control | 0.25c |
| c.1077 | Ex 6 | G > A | A 315 T | MND | 0.0003d |
| c.2076 | 3'UTR | G > A | n/a | MND, FTLD-U | 0.0072e |
| c.3674 | 3'UTR | +/GTTTT | n/a | MND, FTLD-MND, FTLD-U, control | 0.8409f |

(numbering corresponds to polymorphism location with respect to NM_007375); Frequency based on number of chromosomes screened (a) 60/1, 390, (b) 3/276, (c) 19/76, (d) 1/3, 010, (e) 2/276, (f) 37/44). With 276 chromosomes screened and a population frequency of 1%, the power to detect a variant is 0.94.

TABLE 4

Clinical features of a family with MND with a TDP-43 A315T variant.

| Subject | Age at onset/death (years) | Mental status | Cranial nerves | Respiratory involvement | Site of onset | Disease course | Nerve conductions (age performed) | Electromyography |
|---|---|---|---|---|---|---|---|---|
| II-2 | 72/79 | Normal | Normal | Yes | Left lower extremity | Progressive asymmetric lower motor neuron loss in legs before arms, distal before proximal. Brisk reflexes. Death from respiratory weakness. | Normal SNAP amplitudes, normal sensory and motor velocities (72) | Fibs/PSW in legs, thoracic paraspinous muscles. Reduced recruitment. Occasional large motor units. Fasciculations throughout. |

TABLE 4-continued

Clinical features of a family with MND with a TDP-43 A315T variant.

| Subject | Age at onset/ death (years) | Clinical findings | | | | | Electrophysiology | |
| --- | --- | --- | --- | --- | --- | --- | --- | --- |
| | | Mental status | Cranial nerves | Respiratory involvement | Site of onset | Disease course | Nerve conductions (age performed) | Electromyography |
| II-3 | 64/74 | Normal | Normal | Yes | Left lower extremity | Progressive asymmetric lower motor neuron loss in legs before arms, distal and proximal. Brisk reflexes. Death from respiratory weakness. | Normal SNAP amplitudes, normal sensory and motor velocities (68) | Fibs/PSW in legs and arms. Reduced recruitment. Occasional large motor units. Fasciculations throughout. |
| II-4 | 83 | Normal | Normal | Yes | Right lower extremity | Progressive asymmetric lower motor neuron loss, distal and proximal, legs before arms. Brisk reflexes. | Not available | Not available |
| III-1 | 48 | Normal | Normal | No | Right upper extremity | Progressive asymmetric lower motor neuron loss, distal before proximal, arms before legs. | Normal SNAP amplitudes, normal sensory and motor velocities (49) | Fibs/PSW in arms. Fasciculations in arms/legs |

Fibs = fibrillations; PSW = positive sharp waves; SNAP = sensory nerve action potential.

REFERENCES

1. Arai T, Hasegawa M, Akiyama H, et al. Biochem Biophys Res Commun 2006; 351:602-611.
2. Neumann M, Sampathu D M, Kwong L K et al. Science 2006; 314:130-133.
3. Cairns N J, Neumann M, Bigio E H, et al. Am J Pathol 2007; 171:227-240.
4. Mackenzie I R A, Bigio E H, Ince P G, et al. Ann Neurol 2007; 61:427-434.
5. Siddique T, Lalani I. Adv Neurol 2002; 88:21-32.
6. Pasinelli P, Brown R H, Nat Rev Neurosci 2006; 7:710-723.
7. Goate A, Chartier-Harlin M C, Mullan M, et al. Nature 1991; 349:704-706.
8. Polymeropoulos M H, Lavedan C, Leroy E, et al. Science 1997; 276:2045-2047.
9. Hutton M, Lendon C L, Rizzu P, et al. Nature 1998; 393:702-705.
10. Wang H Y, Wang I F, Bose J, Shen C K. Genomics 2004; 83:130-139.
11. Ou S H, Wu F, Harrich D, et al. J Virol 1995; 69:3584-3596.
12. Buratti E, Dork T, Zuccato E. et al. EMBO J 2001; 20:1774-1784.
13. Ayala Y M, Pantano S, D'Ambrogio A. et al. J Mol Biol 2005; 348:575-588.
14. Cairns N J, Bigio E H, Mackenzie I R A, et al. Acta Neuropathol 2007; 114:5-22.
15. Strong M J (ed). 2006. Dementia and Motor Neuron Disease. Informa, Oxford, UK

What is claimed is:

1. An oligonucleotide probe comprising a fragment of a TAR DNA-binding protein 43 (TDP-43) nucleotide sequence or a complement of the TDP-43 nucleotide sequence, wherein the fragment comprises fifteen to 200 contiguous nucleotides of (i) the TDP-43 nucleotide sequence of SEQ ID NO: 1 that includes nucleotide position 1077, wherein the fragment has an A at a position corresponding to nucleotide position 1077 of SEQ ID NO:1, or (ii) a sequence that is complementary to the TDP-43 nucleotide sequence of SEQ ID NO: 1 that includes nucleotide position 1077, wherein the fragment has a T at a position corresponding to nucleotide position 1077 of SEQ ID NO:1, and wherein the oligonucleotide probe is detectably labeled with a fluorescent, chemiluminescent, radioactive, colorimetric, and/or resonance label.

2. The oligonucleotide probe of claim 1, wherein the probe comprises between 15 and 50 nucleotides.

3. An array comprising a substrate, wherein the substrate comprises the oligonucleotide probe of claim 1.

* * * * *

SEQUENCE LISTING

<160> NUMBER OF SEQ ID NOS: 14

<210> SEQ ID NO 1
<211> LENGTH: 4236
<212> TYPE: DNA
<213> ORGANISM: Homo sapiens

<400> SEQUENCE: 1

```
ggtgggcggg gggaggaggc ggccctagcg ccattttgtg ggagcgaagc ggtggctggg      60
ctgcgcttgg gtccgtcgct gcttcggtgt ccctgtcggg cttcccagca gcggcctagc     120
gggaaaagta aaagatgtct gaatatattc gggtaaccga agatgagaac gatgagccca     180
ttgaaatacc atcggaagac gatgggacgg tgctgctctc cacggttaca gcccagtttc     240
caggggcgtg tgggcttcgc tacaggaatc cagtgtctca gtgtatgaga ggtgtccggc     300
tggtagaagg aattctgcat gccccagatg ctggctgggg aaatctggtg tatgttgtca     360
actatccaaa agataacaaa agaaaatgg atgagacaga tgcttcatca gcagtgaaag     420
tgaaaagagc agtccagaaa acatccgatt taatagtgtt gggtctccca tggaaaacaa     480
ccgaacagga cctgaaagag tattttagta cctttggaga agttcttatg gtgcaggtca     540
agaaagatct taagactggt cattcaaagg ggtttggctt tgttcgtttt acggaatatg     600
aaacacaagt gaaagtaatg tcacagcgac atatgataga tggacgatgg tgtgactgca     660
aacttcctaa ttctaagcaa agccaagatg agcctttgag aagcagaaaa gtgtttgtgg     720
ggcgctgtac agaggacatg actgaggatg agctgcggga gttcttctct cagtacgggg     780
atgtgatgga tgtcttcatc cccaagccat tcagggcctt tgcctttgtt acatttgcag     840
atgatcagat tgcgcagtct cttttgtggag aggacttgat cattaaagga atcagcgttc     900
atatatccaa tgccgaacct aagcacaata gcaatagaca gttagaaaga agtggaagat     960
ttggtggtaa tccaggtggc tttgggaatc agggtggatt tggtaatagc agaggggtg    1020 gagctggttt gggaaacaat caaggtagta atatgggtgg tgggatgaac tttggtacgt    1080
tcagcattaa tccagccatg atggctgccg cccaggcagc actacagagc agttggggta    1140
tgatgggcat gttagccagc cagcagaacc agtcaggccc atcgggtaat aaccaaaacc    1200
aaggcaacat gcagagggag ccaaaccagg ccttcggttc tggaaataac tcttatagtg    1260
gctctaattc tggtgcagca attggttggg atcagcatc caatgcaggg tcggcagtg    1320 gttttaatgg aggctttggc tcaagcatgg attctaagtc ttctggctgg ggaatgtaga    1380 cagtgggtt gtggttggtt ggtatagaat ggtgggaatt caaattttc taaactcatg    1440 gtaagtatat tgtaaaatac atatgtacta agaattttca aaattggttt gttcagtgtg    1500
gagtatattc agcagtattt ttgacatttt tctttagaaa aaggaagagc taaaggaatt    1560
ttataagttt tgttacatga aaggttgaaa tattgagtgg ttgaaagtga actgctgttt    1620
gcctgattgg taaaccaaca cactacaatt gatatcaaaa ggtttctcct gtaatatttt    1680
atccctggac ttgtcaagtg aattctttgc atgttcaaaa cggaaccat tgattagaac    1740 tacattcttt accccttgtt ttaatttgaa ccccaccata tggatttttt tccttaagaa    1800
aatctccttt taggagatca tggtgtcaca gtgtttggtt cttttgtttt gttttttaac    1860
acttgtctcc cctcatacac aaaagtacaa tatgaagcct tcatttaatc tctgcagttc    1920
atctcatttc aaatgtttat ggaagaagca cttcattgaa agtagtgctg taaatattct    1980
gccataggaa tactgtctac atgctttctc attcaagaat tcgtcatcac gcatcacagg    2040
ccgcgtcttt gacggtgggt gtcccatttt tatccgctac tctttatttc atggagtcgt    2100
atcaacgcta tgaacgcaag gctgtgatat ggaaccagaa ggctgtctga acttttgaaa    2160
ccttgtgtgg gattgatggt ggtgccgagg catgaaaggc tagtatgagc gagaaaagga    2220 gagcgcgt gcagagactt ggtggtgcat aatggatatt ttttaacttg gcagagatgtg    2280 tctctcaatc ctgtggcttt ggtgagagag tgtgcagaga gcaatgatag caaataatgt    2340
```

```
acgaatgttt tttgcattca aaggacatcc acatctgttg aagacttttt aagtgagttt      2400
ttgttcttag ataacccaca ttagatgaat gtgttaagtg aaatgatact tgtactcccc      2460
ctacccsttt gtcaactgct gtgaatgctg tatggtgtgt gttctcttct gttactgata      2520
tgtaagtgtg gcaatgtgaa ctgaagctga tgggctgaga acatggactg agcttgtggt      2580
gtgctttgca ggaggacttg aagcagagtt caccagtgag ctcaggtgtc tcaaagaagg      2640
gtggaagttc taatgtctgt tagctaccca taagaatgct gtttgctgca gttctgtgtc      2700
ctgtgcttgg atgcttttta taagagttgt cattgttgga aattcttaaa taaaactgat      2760
ttaaataata tgtgtctttg ttttgcagcc ctgaatgcaa agaattcata gcagttaatt      2820
ccccttttt gacccttttg agatggaact ttcataaagt ttcttggcag tagtttattt      2880
tgcttcaaat aaacttattt gaaaagttgt ctcaagtcaa atggattcat cacctgtcat      2940
gcattgacac ctgataccca gacttaattg gtatttgttc ttgcattggc caaagtgaaa      3000
atttttttt ttcttttgaa atctagtttt gaataagtct gggtgaccgc acctaaaatg      3060
gtaagcagta ccctccggct ttttcttagt gcctctgtgc atttgggtga tgttctattt      3120
acatggcctg tgtaaatctc cattgggaag tcatgccttc taaaaagatt cttatttggg      3180
ggagtgggca aaatgttgat tattttctaa tgctttgtag caaagcatat caattgaaaa      3240
gggaatatca gcaccttcct agtttgggat ttgaaaagtg aattaattg cagtagggat       3300
aaagtagaag aaaccacaaa ttatcttgtg cctgaaatcc attaagaggc ctgatagctt      3360
taagaattag ggtgggttgt ctgtctggaa gtgttaagtg aatgggctt tgtcctccag       3420
gaggtggggg aatgtggtaa cattgaatac agttgaataa aatcgcttac aaaactcaca      3480
ctctcacaat gcattgttaa gtatgtaaaa gcaataacat tgattctctg ttgtacttt       3540
ttgtaactaa ttctgtgaga gttgagctca ttttctagtt ggaagaatgt gatatttgtt      3600
gtgttggtag tttacctaat gcccttacct aattagatta tgataaatag gtttgtcatt      3660
ttgcaagtta cataaacatt tatcaatgaa gtcatccttt agacttgtaa tcgccacatt      3720
gtttcattat tcagtttcct ctgtaaaggg atcttgagtt gttttaattt ttttttttctg     3780
catctgaatc tgcatgattt ccaaaccctg taccatctga attttgcatt ttagcacttg      3840
cactattact cagcagcagt aacatggtaa cacttaaaat ggtactcggg gacctccaaa      3900
gactaaactg acaagccttc aaggagccca ggggtaagtt aacttgtcaa cggcatggtt      3960
taatcccttc tttacacttg tgtaaatttc agttactggt catagaaggc tttcaatgtt      4020
gagtggccet ttattaacat gtttatggta ctgcatagat acgggtattt atttttaccct    4080
aagaagattt tgaagtttaa aagtacttaa actatttggc aaagatttgt ttttaaaaat     4140
ctatttggtc aatctaaatg cattcattct aaaaaatttt ttgaaccaga taaataaaat     4200
ttttttttga caccacaaaa aaaaaaaaaa aaaaaa                                4236
```

<210> SEQ ID NO 2
<211> LENGTH: 414
<212> TYPE: PRT
<213> ORGANISM: Homo sapiens
<400> SEQUENCE: 2

```
Met Ser Glu Tyr Ile Arg Val Thr Glu Asp Glu Asn Asp Glu Pro Ile
1               5                   10                  15

Glu Ile Pro Ser Glu Asp Asp Gly Thr Val Leu Leu Ser Thr Val Thr
            20                  25                  30

Ala Gln Phe Pro Gly Ala Cys Gly Leu Arg Tyr Arg Asn Pro Val Ser
```

```
                35                  40                  45
Gln Cys Met Arg Gly Val Arg Leu Val Glu Gly Ile Leu His Ala Pro
 50                  55                  60
Asp Ala Gly Trp Gly Asn Leu Val Tyr Val Asn Tyr Pro Lys Asp
 65                  70                  75                  80
Asn Lys Arg Lys Met Asp Glu Thr Asp Ala Ser Ser Ala Val Lys Val
                 85                  90                  95
Lys Arg Ala Val Gln Lys Thr Ser Asp Leu Ile Val Leu Gly Leu Pro
                100                 105                 110
Trp Lys Thr Thr Glu Gln Asp Leu Lys Glu Tyr Phe Ser Thr Phe Gly
                115                 120                 125
Glu Val Leu Met Val Gln Val Lys Lys Asp Leu Lys Thr Gly His Ser
                130                 135                 140
Lys Gly Phe Gly Phe Val Arg Phe Thr Glu Tyr Glu Thr Gln Val Lys
145                 150                 155                 160
Val Met Ser Gln Arg His Met Ile Asp Gly Arg Trp Cys Asp Cys Lys
                165                 170                 175
Leu Pro Asn Ser Lys Gln Ser Gln Asp Glu Pro Leu Arg Ser Arg Lys
                180                 185                 190
Val Phe Val Gly Arg Cys Thr Glu Asp Met Thr Glu Asp Glu Leu Arg
                195                 200                 205
Glu Phe Phe Ser Gln Tyr Gly Asp Val Met Asp Val Phe Ile Pro Lys
                210                 215                 220
Pro Phe Arg Ala Phe Ala Phe Val Thr Phe Ala Asp Asp Gln Ile Ala
225                 230                 235                 240
Gln Ser Leu Cys Gly Glu Asp Leu Ile Ile Lys Gly Ile Ser Val His
                245                 250                 255
Ile Ser Asn Ala Glu Pro Lys His Asn Ser Asn Arg Gln Leu Glu Arg
                260                 265                 270
Ser Gly Arg Phe Gly Gly Asn Pro Gly Gly Phe Gly Asn Gln Gly Gly
                275                 280                 285
Phe Gly Asn Ser Arg Gly Gly Gly Ala Gly Leu Gly Asn Asn Gln Gly
                290                 295                 300
Ser Asn Met Gly Gly Gly Met Asn Phe Gly Thr Phe Ser Ile Asn Pro
305                 310                 315                 320
Ala Met Met Ala Ala Ala Gln Ala Ala Leu Gln Ser Ser Trp Gly Met
                325                 330                 335
Met Gly Met Leu Ala Ser Gln Gln Asn Gln Ser Gly Pro Ser Gly Asn
                340                 345                 350
Asn Gln Asn Gln Gly Asn Met Gln Arg Glu Pro Asn Gln Ala Phe Gly
                355                 360                 365
Ser Gly Asn Asn Ser Tyr Ser Gly Ser Asn Ser Gly Ala Ala Ile Gly
                370                 375                 380
Trp Gly Ser Ala Ser Asn Ala Gly Ser Gly Ser Gly Phe Asn Gly Gly
385                 390                 395                 400
Phe Gly Ser Ser Met Asp Ser Lys Ser Ser Gly Trp Gly Met
                405                 410

<210> SEQ ID NO 3
<211> LENGTH: 4236
<212> TYPE: DNA
<213> ORGANISM: Homo sapiens

<400> SEQUENCE: 3
```

```
ggtgggcggg gggaggaggc ggccctagcg ccattttgtg ggagcgaagc ggtggctggg      60
ctgcgcttgg gtccgtcgct gcttcggtgt ccctgtcggg cttcccagca gcggcctagc     120
gggaaaagta aaagatgtct gaatatattc gggtaaccga agatgagaac gatgagccca     180
ttgaaatacc atcggaagac gatgggacgg tgctgctctc cacgttaca gcccagtttc      240
caggggcgtg tgggcttcgc tacaggaatc cagtgtctca gtgtatgaga ggtgtccggc     300
tggtagaagg aattctgcat gccccagatg ctggctgggg aaatctggtg tatgttgtca     360
actatccaaa agataacaaa agaaaatgg atgagacaga tgcttcatca gcagtgaaag      420
tgaaaagagc agtccagaaa acatccgatt aatagtgtt gggtctccca tggaaaacaa      480
ccgaacagga cctgaaagag tattttagta cctttggaga agttcttatg gtgcaggtca     540
agaaagatct taagactggt cattcaaagg ggtttggctt tgttcgtttt acggaatatg     600
aaacacaagt gaaagtaatg tcacagcgac atatgataga tggacgatgg tgtgactgca     660
aacttcctaa ttctaagcaa agccaagatg agcctttgag aagcagaaaa gtgtttgtgg     720
ggcgctgtac agaggacatg actgaggatg agctgcggga gttcttctct cagtacgggg     780
atgtgatgga tgtcttcatc cccaagccat tcagggcctt tgcctttgtt acatttgcag     840
atgatcagat tgcgcagtct cttttgtggag aggacttgat cattaaagga atcagcgttc     900
atatatccaa tgccgaacct aagcacaata gcaatagaca gttagaaaga agtggaagat     960
ttggtggtaa tccaggtggc tttgggaatc agggtgatt tggtaatagc agaggggtg     1020
gagctggttt gggaaacaat caaggtagta atatgggtgg tgggatgaac tttggtgcgt    1080
tcagcattaa tccagccatg atggctgccg cccaggcagc actacagagc agttggggta    1140
tgatgggcat gttagccagc cagcagaacc agtcaggccc atcgggtaat aaccaaaacc    1200
aaggcaacat gcagagggag ccaaaccagg ccttcggttc tggaaataac tcttatagtg    1260
gctctaattc tggtgcagca attggttggg gatcagcatc caatgcaggg tcgggcagtg    1320
gttttaatgg aggctttggc tcaagcatgg attctaagtc ttctggctgg ggaatgtaga    1380
cagtggggtt gtggttggtt ggtatagaat ggtgggaatt caaattttc taaactcatg    1440
gtaagtatat tgtaaaatac atatgtacta agaattttca aaattggttt gttcagtgtg    1500
gagtatattc agcagtattt ttgacatttt tctttagaaa aaggaagagc taaggaatt    1560
ttataagttt tgttacatga aaggttgaaa tattgagtgg ttgaaagtga actgctgttt    1620
gcctgattgg taaaccaaca cactacaatt gatatcaaaa ggtttctcct gtaatatttt    1680
atccctggac ttgtcaagtg aattctttgc atgttcaaaa cggaaaccat tgattagaac    1740
tacattcttt acccttgtt ttaatttgaa ccccaccata tggatttttt tccttaagaa     1800
aatctccttt taggagatca tggtgtcaca gtgtttggtt cttttgtttt gttttttaac    1860
acttgtctcc cctcatacac aaaagtacaa tatgaagcct tcatttaatc tctgcagttc    1920
atctcatttc aaatgtttat ggaagaagca cttcattgaa agtagtgctg taaatattct    1980
gccataggaa tactgtctac atgctttctc attcaagaat tcgtcatcac gcatcacagg    2040
ccgcgtcttt gacggtgggt gtcccatttt tatccgctac tctttatttc atggagtcgt    2100
atcaacgcta tgaacgcaag gctgtgtatat ggaaccagaa ggctgtctga acttttgaaa    2160
ccttgtgtgg gattgatggt ggtgccgagg catgaaaggc tagtatgagc gagaaaagga    2220
gagagcgcgt gcagagactt ggtggtgcat aatggatatt ttttaacttg gcgagatgtg    2280
tctctcaatc ctgtggcttt ggtgagagag tgtgcagaga gcaatgatag caaataatgt    2340
acgaatgttt tttgcattca aaggacatcc acatctgttg gaagactttt aagtgagttt    2400
```

```
ttgttcttag ataacccaca ttagatgaat gtgttaagtg aaatgatact tgtactcccc    2460 ctacccctttt gtcaactgct gtgaatgctg tatggtgtgt gttctcttct gttactgata    2520
tgtaagtgtg gcaatgtgaa ctgaagctga tgggctgaga acatggactg agcttgtggt    2580
gtgctttgca ggaggacttg aagcagagtt caccagtgag ctcaggtgtc tcaaagaagg    2640
gtggaagttc taatgtctgt tagctaccca taagaatgct gttttgctgca gttctgtgtc    2700 ctgtgcttgg atgcttttta taagagttgt cattgttgga aattcttaaa taaaactgat    2760
ttaaataata tgtgtctttg ttttgcagcc ctgaatgcaa agaattcata gcagttaatt    2820 ccccttttt gaccctttg agatggaact ttcataaagt ttcttggcag tagttttattt    2880 tgcttcaaat aaacttattt gaaaagttgt ctcaagtcaa atggattcat cacctgtcat    2940
gcattgacac ctgatatccca gacttaattg gtatttgttc ttgcattggc caaagtgaaa    3000
attttttttt ttcttttgaa atctagtttt gaataagtct gggtgaccgc acctaaaatg    3060
gtaagcagta ccctccggct tttttcttagt gcctctgtgc atttgggtga tgttctattt    3120
acatggcctg tgtaaatctc cattgggaag tcatgccttc taaaaagatt cttatttggg    3180
ggagtgggca aaatgttgat tattttctaa tgctttgtag caaagcatat caattgaaaa    3240
gggaatatca gcaccttcct agtttgggat ttgaaaagtg gaattaattg cagtagggat    3300
aaagtagaag aaaccacaaa ttatcttgtg cctgaaatcc attaagaggc ctgatagctt    3360
taagaattag ggtgggttgt ctgtctggaa gtgttaagtg gaatgggctt tgtcctccag    3420
gaggtggggg aatgtggtaa cattgaatac agttgaataa aatcgcttac aaaactcaca    3480
ctctcacaat gcattgttaa gtatgtaaaa gcaataacat tgattctctg ttgtactttt    3540
ttgtaactaa ttctgtgaga gttgagctca ttttctagtt ggaagaatgt gatatttgtt    3600
gtgttggtag tttacctaat gcccttacct aattagatta tgataaatag gtttgtcatt    3660
ttgcaagtta cataaacatt tatcaatgaa gtcatccttt agacttgtaa tcgccacatt    3720
gtttcattat tcagtttcct ctgtaaaggg atcttgagtt gttttaattt tttttttctg    3780
catctgaatc tgcatgattt ccaaaccctg taccatctga attttgcatt ttagcacttg    3840
cactattact cagcagcagt aacatggtaa cacttaaaat ggtactcggg gacctccaaa    3900
gactaaactg acaagccttc aaggagccca ggggtaagtt aacttgtcaa cggcatggtt    3960
taatcccttc tttacacttg tgtaaatttc agttactggt catagaaggc tttcaatgtt    4020
gagtggcctt ttattaacat gtttatggta ctgcatagat acgggtattt attttaccct    4080
aagaagattt tgaagtttaa aagtacttaa actatttggc aaagatttgt ttttaaaaat    4140
ctatttggtc aatctaaatg cattcattct aaaaaatttt ttgaaccaga taaataaaat    4200 tttttttga caccacaaaa aaaaaaaaaa aaaaaa                               4236
```

<210> SEQ ID NO 4
<211> LENGTH: 414
<212> TYPE: PRT
<213> ORGANISM: Homo sapiens

<400> SEQUENCE: 4

Met Ser Glu Tyr Ile Arg Val Thr Glu Asp Glu Asn Asp Glu Pro Ile
1               5                   10                  15

Glu Ile Pro Ser Glu Asp Asp Gly Thr Val Leu Leu Ser Thr Val Thr
            20                  25                  30

Ala Gln Phe Pro Gly Ala Cys Gly Leu Arg Tyr Arg Asn Pro Val Ser
        35                  40                  45

```
Gln Cys Met Arg Gly Val Arg Leu Val Glu Gly Ile Leu His Ala Pro
 50                  55                  60

Asp Ala Gly Trp Gly Asn Leu Val Tyr Val Asn Tyr Pro Lys Asp
 65                  70                  75                  80

Asn Lys Arg Lys Met Asp Glu Thr Asp Ala Ser Ser Ala Val Lys Val
                 85                  90                  95

Lys Arg Ala Val Gln Lys Thr Ser Asp Leu Ile Val Leu Gly Leu Pro
            100                 105                 110

Trp Lys Thr Thr Glu Gln Asp Leu Lys Glu Tyr Phe Ser Thr Phe Gly
        115                 120                 125

Glu Val Leu Met Val Gln Val Lys Lys Asp Leu Lys Thr Gly His Ser
130                 135                 140

Lys Gly Phe Gly Phe Val Arg Phe Thr Glu Tyr Glu Thr Gln Val Lys
145                 150                 155                 160

Val Met Ser Gln Arg His Met Ile Asp Gly Arg Trp Cys Asp Cys Lys
                165                 170                 175

Leu Pro Asn Ser Lys Gln Ser Gln Asp Glu Pro Leu Arg Ser Arg Lys
            180                 185                 190

Val Phe Val Gly Arg Cys Thr Glu Asp Met Thr Glu Asp Glu Leu Arg
        195                 200                 205

Glu Phe Phe Ser Gln Tyr Gly Asp Val Met Asp Val Phe Ile Pro Lys
210                 215                 220

Pro Phe Arg Ala Phe Ala Phe Val Thr Phe Ala Asp Asp Gln Ile Ala
225                 230                 235                 240

Gln Ser Leu Cys Gly Glu Asp Leu Ile Ile Lys Gly Ile Ser Val His
                245                 250                 255

Ile Ser Asn Ala Glu Pro Lys His Asn Ser Asn Arg Gln Leu Glu Arg
            260                 265                 270

Ser Gly Arg Phe Gly Gly Asn Pro Gly Gly Phe Gly Asn Gln Gly Gly
        275                 280                 285

Phe Gly Asn Ser Arg Gly Gly Gly Ala Gly Leu Gly Asn Asn Gln Gly
290                 295                 300

Ser Asn Met Gly Gly Gly Met Asn Phe Gly Ala Phe Ser Ile Asn Pro
305                 310                 315                 320

Ala Met Met Ala Ala Ala Gln Ala Ala Leu Gln Ser Ser Trp Gly Met
                325                 330                 335

Met Gly Met Leu Ala Ser Gln Gln Asn Gln Ser Gly Pro Ser Gly Asn
            340                 345                 350

Asn Gln Asn Gln Gly Asn Met Gln Arg Glu Pro Asn Gln Ala Phe Gly
        355                 360                 365

Ser Gly Asn Asn Ser Tyr Ser Gly Ser Asn Ser Gly Ala Ala Ile Gly
370                 375                 380

Trp Gly Ser Ala Ser Asn Ala Gly Ser Gly Ser Gly Phe Asn Gly Gly
385                 390                 395                 400

Phe Gly Ser Ser Met Asp Ser Lys Ser Ser Gly Trp Gly Met
                405                 410

<210> SEQ ID NO 5
<211> LENGTH: 50
<212> TYPE: PRT
<213> ORGANISM: Homo sapiens

<400> SEQUENCE: 5

Asn Ser Arg Gly Gly Gly Ala Gly Leu Gly Asn Asn Gln Gly Ser Asn
```

```
                1               5                   10                  15
Met Gly Gly Gly Met Asn Phe Gly Ala Phe Ser Ile Asn Pro Ala Met
                    20                  25                  30

Met Ala Ala Ala Gln Ala Ala Leu Gln Ser Ser Trp Gly Met Met Gly
            35                  40                  45

Met Leu
    50

<210> SEQ ID NO 6
<211> LENGTH: 50
<212> TYPE: PRT
<213> ORGANISM: Pan troglodytes

<400> SEQUENCE: 6

Asn Ser Arg Gly Gly Gly Ala Gly Leu Gly Asn Asn Gln Gly Ser Asn
1               5                   10                  15

Met Gly Gly Gly Met Asn Phe Gly Ala Phe Ser Ile Asn Pro Ala Met
                    20                  25                  30

Met Ala Ala Ala Gln Ala Ala Leu Gln Ser Ser Trp Gly Met Met Gly
            35                  40                  45

Met Leu
    50

<210> SEQ ID NO 7
<211> LENGTH: 50
<212> TYPE: PRT
<213> ORGANISM: Macaca mulatta

<400> SEQUENCE: 7

Asn Ser Arg Gly Gly Gly Ala Gly Leu Gly Asn Asn Gln Gly Ser Asn
1               5                   10                  15

Met Gly Gly Gly Met Asn Phe Gly Ala Phe Ser Ile Asn Pro Ala Met
                    20                  25                  30

Met Ala Ala Ala Gln Ala Ala Leu Gln Ser Ser Trp Gly Met Met Gly
            35                  40                  45

Met Leu
    50

<210> SEQ ID NO 8
<211> LENGTH: 50
<212> TYPE: PRT
<213> ORGANISM: Bos taurus

<400> SEQUENCE: 8

Asn Ser Arg Gly Gly Gly Ala Gly Leu Gly Asn Asn Gln Gly Ser Asn
1               5                   10                  15

Met Gly Gly Gly Met Asn Phe Gly Ala Phe Ser Ile Asn Pro Ala Met
                    20                  25                  30

Met Ala Ala Ala Gln Ala Ala Leu Gln Ser Ser Trp Gly Met Met Gly
            35                  40                  45

Met Leu
    50

<210> SEQ ID NO 9
<211> LENGTH: 50
<212> TYPE: PRT
<213> ORGANISM: Felis catus

<400> SEQUENCE: 9
```

```
Asn Ser Arg Gly Gly Gly Ala Gly Leu Gly Asn Asn Gln Gly Ser Asn
1               5                   10                  15

Met Gly Gly Gly Met Asn Phe Gly Ala Phe Ser Ile Asn Pro Ala Met
            20                  25                  30

Met Ala Ala Ala Gln Ala Ala Leu Gln Ser Ser Trp Gly Met Met Gly
        35                  40                  45

Met Leu
    50
```

<210> SEQ ID NO 10
<211> LENGTH: 49
<212> TYPE: PRT
<213> ORGANISM: Cavia porcellus

<400> SEQUENCE: 10

```
Asn Arg Gly Gly Gly Ala Gly Leu Gly Asn Asn Gln Gly Ser Asn Met
1               5                   10                  15

Gly Gly Gly Met Asn Phe Gly Ala Phe Ser Ile Asn Pro Ala Met Met
            20                  25                  30

Ala Ala Ala Gln Ala Ala Leu Gln Ser Ser Trp Gly Met Met Gly Met
        35                  40                  45

Leu
```

<210> SEQ ID NO 11
<211> LENGTH: 50
<212> TYPE: PRT
<213> ORGANISM: Rattus norvegicus

<400> SEQUENCE: 11

```
Asn Ser Arg Gly Gly Gly Ala Gly Leu Gly Asn Asn Gln Gly Gly Asn
1               5                   10                  15

Met Gly Gly Gly Met Asn Phe Gly Ala Phe Ser Ile Asn Pro Ala Met
            20                  25                  30

Met Ala Ala Ala Gln Ala Ala Leu Gln Ser Ser Trp Gly Met Met Gly
        35                  40                  45

Met Leu
    50
```

<210> SEQ ID NO 12
<211> LENGTH: 50
<212> TYPE: PRT
<213> ORGANISM: Mus musculus

<400> SEQUENCE: 12

```
Asn Ser Arg Gly Gly Gly Ala Gly Leu Gly Asn Asn Gln Gly Gly Asn
1               5                   10                  15

Met Gly Gly Gly Met Asn Phe Gly Ala Phe Ser Ile Asn Pro Ala Met
            20                  25                  30

Met Ala Ala Ala Gln Ala Ala Leu Gln Ser Ser Trp Gly Met Met Gly
        35                  40                  45

Met Leu
    50
```

<210> SEQ ID NO 13
<211> LENGTH: 50
<212> TYPE: PRT
<213> ORGANISM: Gallus gallus

<400> SEQUENCE: 13

-continued

```
Asn Ser Arg Gly Gly Gly Gly Leu Gly Asn Asn Gln Gly Ser Asn
1               5                   10                  15

Met Gly Gly Gly Met Asn Phe Gly Ala Phe Ser Ile Asn Pro Ala Met
            20                  25                  30

Met Ala Ala Ala Gln Ala Ala Leu Gln Ser Ser Trp Gly Met Met Gly
        35                  40                  45

Met Leu
    50

<210> SEQ ID NO 14
<211> LENGTH: 52
<212> TYPE: PRT
<213> ORGANISM: Xenopus tropicalis

<400> SEQUENCE: 14

Asn Ser Arg Pro Ser Ser Gly Ala Leu Gly Asn Asn Gln Gly Gly Asn
1               5                   10                  15

Met Gly Gly Gly Gly Gly Met Asn Phe Gly Ala Phe Ser Ile Asn Pro
            20                  25                  30

Ala Met Met Ala Ala Ala Gln Ala Ala Leu Gln Ser Ser Trp Gly Met
        35                  40                  45

Met Gly Met Leu
    50
```